United States Patent
Hiban et al.

(10) Patent No.: US 11,904,035 B2
(45) Date of Patent: Feb. 20, 2024

(54) LAMELLAR LIQUID CLEANSERS COMPRISING ACYL ISETHIONATE AND METHYL ACYL TAURATE SURFACTANT MIXTURES

(71) Applicant: Conopco, Inc., Englewood Cliffs, NJ (US)

(72) Inventors: Douglas John Hiban, Shelton, CT (US); Jamie Lynn Miller, North Haven, CT (US); Tirucherai Varahan Vasudevan, Bethany, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 94 days.

(21) Appl. No.: 17/611,700

(22) PCT Filed: May 4, 2020

(86) PCT No.: PCT/EP2020/062329
§ 371 (c)(1),
(2) Date: Nov. 16, 2021

(87) PCT Pub. No.: WO2020/233972
PCT Pub. Date: Nov. 26, 2020

(65) Prior Publication Data
US 2022/0192934 A1    Jun. 23, 2022

(30) Foreign Application Priority Data
May 21, 2019    (EP) .................................... 19175537

(51) Int. Cl.
| | |
|---|---|
| A61K 8/00 | (2006.01) |
| A61K 8/02 | (2006.01) |
| A61K 8/34 | (2006.01) |
| A61K 8/36 | (2006.01) |
| A61K 8/365 | (2006.01) |
| A61K 8/44 | (2006.01) |
| A61K 8/46 | (2006.01) |
| A61Q 5/02 | (2006.01) |
| A61Q 19/10 | (2006.01) |

(52) U.S. Cl.
CPC ............ *A61K 8/0295* (2013.01); *A61K 8/345* (2013.01); *A61K 8/361* (2013.01); *A61K 8/365* (2013.01); *A61K 8/442* (2013.01); *A61K 8/466* (2013.01); *A61Q 5/02* (2013.01); *A61Q 19/10* (2013.01); *A61K 2800/596* (2013.01)

(58) Field of Classification Search
CPC ....... A61K 8/0295; A61K 8/442; A61K 8/466
See application file for complete search history.

(56) References Cited

U.S. PATENT DOCUMENTS

| | | |
|---|---|---|
| 5,415,810 A | 5/1995 | Lee |
| 5,925,603 A | 7/1999 | D'Angelo |
| 6,562,874 B1 | 5/2003 | Ilardi et al. |
| 9,187,716 B2 | 11/2015 | Griffin et al. |
| 2002/0009484 A1 | 1/2002 | McAtee |
| 2005/0143269 A1 | 6/2005 | Wei et al. |
| 2007/0141001 A1 | 6/2007 | Clapp et al. |
| 2008/0095733 A1 | 4/2008 | Griffin et al. |
| 2009/0062406 A1 | 3/2009 | Loeffler |
| 2012/0141389 A1 | 6/2012 | Cotrell et al. |
| 2014/0349902 A1* | 11/2014 | Allef ...................... A61Q 19/10 510/491 |
| 2015/0157540 A1 | 6/2015 | Rizk et al. |
| 2015/0297489 A1* | 10/2015 | Kleinen ................ A61Q 19/10 510/130 |
| 2016/0095804 A1 | 4/2016 | Xavier et al. |
| 2017/0196780 A1 | 7/2017 | Mizuno et al. |
| 2017/0304173 A1 | 10/2017 | Elder |
| 2018/0071198 A1* | 3/2018 | Lin ........................ A61K 8/85 |
| 2018/0318195 A1 | 11/2018 | Blachechen et al. |
| 2019/0060200 A1 | 2/2019 | Adamy et al. |
| 2019/0247286 A1 | 8/2019 | Watanabe et al. |
| 2019/0365623 A1 | 12/2019 | Botto et al. |
| 2020/0030208 A1 | 1/2020 | Meyers et al. |
| 2020/0170894 A1 | 6/2020 | Park et al. |
| 2021/0113443 A1 | 4/2021 | Borish et al. |
| 2021/0196604 A1 | 7/2021 | Rowney et al. |
| 2021/0299020 A1 | 9/2021 | Cruz et al. |
| 2021/0401716 A1 | 12/2021 | Gogineni et al. |
| 2022/0395444 A1 | 12/2022 | Hutton, III |
| 2023/0089228 A1 | 3/2023 | Deng et al. |

(Continued)

FOREIGN PATENT DOCUMENTS

| | | |
|---|---|---|
| CN | 1897909 | 1/2007 |
| CN | 101330895 | 1/2007 |
| CN | 101375826 | 3/2009 |

(Continued)

OTHER PUBLICATIONS

Search Report and Written Opinion in EP19175537; dated Jul. 12, 2019.
Search Report and Written Opinoin in EP19175538; dated Aug. 27, 2019.
Search Report & Written Opinion in PCTEP2020062329; dated Jul. 15, 2020.
Search Report & Written Opinion in PCTEP2020062328; dated Jul. 28, 2020.
IPRP2 in PCTEP2020062328; Aug. 13, 2021.
IPRP2 in PCTEP2020062329; Aug. 10, 2021.

(Continued)

*Primary Examiner* — Necholus Ogden, Jr.
(74) *Attorney, Agent, or Firm* — Edward A. Squillante, Jr.

(57) ABSTRACT

The invention relates to lamellar liquid composition comprising acyl isethionate, methyl acyl taurate, amphoteric and/or zwitterionic surfactant. Unexpectedly, applicants have found that, when ratio of isethionate to taurate is kept at about to 1:1, enhanced lather is achieved. Other criticalities include ratio of amphoteric and/or zwitterionic to anionic surfactant, total amount of surfactant, and pH.

19 Claims, No Drawings

(56) References Cited

U.S. PATENT DOCUMENTS

| | | | |
|---|---|---|---|
| 2023/0113844 A1 | 4/2023 | Cochran et al. | |
| 2023/0114446 A1 | 4/2023 | Cochran et al. | |

FOREIGN PATENT DOCUMENTS

| | | |
|---|---|---|
| CN | 108697608 | 4/2022 |
| WO | WO2014201541 | 12/2014 |
| WO | WO2015089259 | 6/2015 |
| WO | WO2017140799 | 8/2017 |
| WO | WO2019000407 | 1/2019 |
| WO | WO2019011521 | 1/2019 |
| WO | WO2020043336 | 3/2020 |
| WO | WO2020099036 | 5/2020 |
| WO | WO2020229097 | 11/2020 |
| ZA | 9808057 | 2/1999 |

OTHER PUBLICATIONS

Co-pending U.S. Appl. No. 17/611,705, filed Nov. 16, 2021 entitled Isotropic Liquid Cleansers Comprising Acyl Isethionate and Methyl Acyl Taurate Surfactant Mixtures.

* cited by examiner

LAMELLAR LIQUID CLEANSERS COMPRISING ACYL ISETHIONATE AND METHYL ACYL TAURATE SURFACTANT MIXTURES

FIELD OF THE INVENTION

The present invention relates to lamellar liquid cleansing compositions suitable for topical application for cleansing the human body, such as skin and hair. In particular, it relates to compositions which, at least in one embodiment, are preferably sulfate free and mild on the skin and scalp. The compositions preferably are able to lather appreciably, are stable and have a lamellar (liquid crystalline) microstructure.

BACKGROUND OF THE INVENTION

Consumers seek sulfate free personal cleansing compositions (e.g., having no sulfate-based surfactants) that are extremely mild and moisturizing while delivering superior sensory benefits such as creamy lather and soft, smooth skin typically after one shower. Acyl isethionates are known to be extremely mild surfactants and are an ideal surfactant for delivering mildness and moisturization with voluminous and creamy lather that consumers desire. However, liquid cleansers containing high levels of acyl isethionates tend to crystallize due to the low solubility of acyl isethionates in aqueous systems.

Lamellar liquids are enjoyed by consumers since they have a justifiable reputation for being a moisturizing body wash, given their lotion like consistency. In addition, high emollient loadings can be achieved in a lamellar body wash compositions without destabilizing such compositions.

Sun et al (Journal of Cosmetic Science, 54, 559-568, 2003) have suggested several surfactants that can be used to solubilize acyl isethionates such as methyl acyl taurates, acyl glutamates, acyl lactylates, alkyl ether and dialkyl sulfosuccinates, and acyl sarcosinates. Among the surfactants outlined, methyl acyl taurate offers a distinct advantage over the others in that methyl acyl taurates and acyl isethionates can be commercially synthesized as a mixture in a single pot reactor (U.S. Pat. No. 6,562,874 to Ilardi et al.).

In the present invention, unexpectedly, it has been found that a mixture of acyl isethionate and methyl acyl taurate, when combined in a specific weight ratio, exhibit synergy and generate a superior and enhanced lather volume, while maintaining lather creaminess, attributes which are desired by consumers.

U.S. Pat. No. 5,415,810 to Lee et al. discloses acyl isethionate containing liquids that also contain other anionic surfactants such as methyl acyl taurates, but there is no recognition of any synergy (e.g., in lather) between acyl isethionates and methyl acyl taurates used in a specific range of ratio between the two surfactants.

U.S. Pat. No. 5,925,603 to D'Angelo discloses the use of methyl acyl taurate as a solubilizing surfactant for acyl isethionates, but there is no recognition that specific ratios of acyl isethionate to methyl acyl taurate can produce synergistic lather performance. The disclosed compositions are also stipulated to be between 7.5 and 8.5 pH units. At these pH values, acyl isethionates can undergo hydrolysis when held at the type of higher temperatures that are quite prevalent in tropical regions. It is most desirable to formulate acyl isethionate formulations between pH 6 to 7.3 to avoid hydrolysis. Formulations of the subject invention have a pH of 5.0 to 7.4, preferably 6.0 to 7.3. In preferred embodiments, composition pH is 6.3 to 7.0

US 2009/0062406 A1 to Loeffler et al. discloses flowable aqueous concentrates comprising a mixture of acyl isethionate, methyl acyl taurate and alkyl betaines. Here again, there is no recognition that specific ratios between acyl isethionate and methyl acyl taurate can be synergistic in terms of generating consumer desired lather. The compositions are concentrated systems with surfactant levels well above 20%. Compositions of the invention have surfactant levels below 20% by weight.

Lamellar liquid crystalline compositions comprising mixtures of isethionate surfactants, taurate surfactants and sarcosinate surfactants are disclosed in U.S. Pat. No. 9,187,716 to Griffin et al. The compositions described comprise at least 2% by weight electrolyte, and enhanced lather volume and maintenance of lather creaminess attributes are not recognized. Further, the amount of isethionate is greater than 3 times the amount of taurate in the examples (Examples 1-A, 2-A).

US 2017/0304173 to Elder et al. discloses compositions for make-up removal that comprise mixtures of acyl isethionate and methyl acyl taurates. Again, there is no recognition that specific ratios between acyl isethionate and methyl acyl taurate can be synergistic in terms of generating consumer desired lather. Additionally, the disclosed compositions require use of non-ionic emulsifiers which are efficacious for removing make up.

However, use of nonionic emulsifiers is optional in the mild skin and hair cleansing (lamellar) compositions of the present invention. In an embodiment of the invention, compositions (or formulations) are substantially free of nonionic emulsifiers (or surfactants) where substantially free means less than 0.01 percent by weight based on total weight of the composition. In another embodiment, the composition of the present invention comprises less than 0.008% and in still another embodiment less than 0.005% by weight nonionic emulsifier based on total weight of the composition. In still another embodiment, the composition of the present invention comprises from 0.00001 to 0.004% by weight nonionic emulsifier. In yet another embodiment, the composition is free of (0.0%) nonionic emulsifier. In still another embodiment, the composition of this invention is substantially free of nonionic emulsifier when amphoteric surfactant (including betaines), zwitterionic surfactant or a mixture thereof are present at 0.1% by weight or more of the total weight of the composition. When betaine, zwitterionic and/or amphoteric surfactant (including betaines) do not exceed 0.1% by weight of the composition, it is within the scope of the invention for the composition to comprise from 0.00001 to 8% by weight nonionic surfactant, including all ranges subsumed therein, and in another embodiment, from 0.001 to 7% by weight nonionic surfactant and in still another embodiment, from 1 to 6% by weight nonionic surfactant.

Unexpectedly, it has been found that when the ratio of acyl isethionate to methyl acyl taurate is controlled (1.5:1 to 1:1.5), a significant boost in lather volume is obtained.

BRIEF DESCRIPTION OF THE INVENTION

The present invention is directed to a lamellar personal cleansing liquid composition. Lamellar compositions are those in which surfactant micelles aggregate and form liquid crystalline surfactant bilayers. The composition comprises:
1) 0.1 to 10%, preferably 0.5 to 8%, more preferably 1 to 6% by weight of acyl isethionate;

2) 0.1% to 10%, preferably 0.5 to 8%, more preferably 1 to 6% by weight of methyl acyl taurate;
3) 0.1 to 20%, preferably 1 to 10%, more preferably 2 to 5% by weight lamellar structurant;
4) 0.0 to 15%, preferably 0.1 to 10% and more preferably 0.5 to 8% by weight of an amphoteric and/or zwitterionic surfactant; and
5) 0.0 to 8.0%, preferably 0.001 to 7%, and more preferably, 1 to 6% by weight nonionic surfactant, with the proviso that total surfactant is at a sum of less than 20% by weight and the composition does not simultaneously comprise 0.01% by weight or more nonionic surfactant and 0.1% by weight or more amphoteric surfactant (including betaine) and/or zwitterionic surfactant and does not simultaneously comprise 0.0% by weight amphoteric and/or zwitterionic surfactant and 0.0% by weight nonionic surfactant, wherein the ratio of acyl isethionate to methyl acyl taurate surfactant is between 1.5:1 to 1:1.5, and preferably, from 1.25:1 to 1:1.25, and more preferably, 1.1:1 to 1:1.1, and most preferably, 1:1.

In an embodiment of the invention, the ratio of amphoteric, zwitterionic and/or nonionic to anionic surfactant is 1:10 to 4:1, preferably 1:8 to 3:1, and most preferably, from 1:5 to 2:1 with the proviso that sum of all the surfactants is, again, less than 20% by weight, and that the composition pH is 5.0 to 7.4, and preferably, 6.0 to 7.3 and further wherein the composition is substantially free of nonionic surfactant. In some embodiments, pH of the composition is 6.3 to 7.3, including all ranges subsumed therein. In an especially preferred embodiment, the ratio of amphoteric and/or zwitterionic to anionic is 1:1.

In still another embodiment of the invention amphoteric and/or zwitterionic surfactant make(s) up from 0.0 to less than 0.1% by weight of the composition and nonionic surfactant is present at an amount from 0.02 to 8% by weight of the composition.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about."

As used throughout, ranges are used as shorthand for describing each and every value that is within the range. Any value within the range can be selected as terminus of the range. Therefore, all ranges are meant to include all ranges subsumed therein. The use of and/or indicates that any one from the list can be chosen individually, or any combination from the list can be chosen.

For the avoidance of doubt, the word "comprising" is intended to mean "including" but not necessarily "consisting of" or "composed of." In other words, the listed steps or options need not be exhaustive. Lamellar Structuring agent is meant to include fatty acids, liquid alcohols and derivatives thereof (e.g., ester derivatives), all of which induce a lamellar phase in a personal care composition.

Unless indicated otherwise, all percentages for amount or amounts of ingredients used are to be understood to be percentages by weight based on the active weight of the material in the total weight of the composition, which total is 100%. Emulsifier and surfactant can be used interchangeably herein. For the avoidance of doubt, amphoteric surfactants include betaines. Nonionic surfactant, as used herein, includes amine oxides.

The present invention relates to lamellar liquid cleansing compositions comprising acyl isethionate, methyl acyl taurate, and at least one of, an amphoteric, zwitterionic and/or nonionic surfactant. Lamellar compositions are those in which the surfactants form micelles that do aggregate to form lamellar (liquid crystalline) layers. The invention relates to lamellar cleansing compositions comprising less than 0.2% by weight sulfate based surfactant. In another embodiment, the invention is directed to a composition comprising from 0.0001 to less than 0.2% by weight sulfate based surfactant. In still another embodiment, the invention is directed to a composition having no (0.0% by weight) sulfate based surfactant. In still another embodiment of the invention, the composition comprises less than 3% by weight betaine. In still another embodiment, the composition of this invention comprises from 0.0001 to 2.5% by weight betaine and yet in another embodiment no (0.0% by weight) betaine.

When the acyl isethionate and acyl methyl taurate are kept within a ratio of 1.5:1 to 1:1.5; the overall level of surfactants is kept at less than 20% by weight of the composition; and the pH is at 5.0 to 7.4, preferably 6.0 to 7.3, the benefits of mildness are produced and maintained by the composition of the present invention while significantly enhancing lather compared to compositions where ratio of acyl isethionate to methyl acyl taurate is outside these ranges. The compositions may optionally comprise amphoteric, zwitterionic and/or nonionic surfactant and the ratio of such surfactant to anionic surfactant can be 1:1 and higher.

More specifically, the invention comprises:
1) 0.1 to 8%, preferably 0.5 to 6%, more preferably 1 to 4% by weight acyl isethionate;
2) 0.1% to 8%, preferably 0.5 to 6%, more preferably 1 to 4% by weight of methyl acyl taurate;
3) 0.1 to 20%, preferably 1 to 10%, more preferably 2 to 5% by weight lamellar structurant;
4) 0.1 to 8%, preferably 0.2 to 7% and more preferably 1 to 6% by weight of an amphoteric and/or zwitterionic surfactant; and
5) 0.0 to 8.0%, preferably 0.001 to 7%, and more preferably, 1 to 6% by weight nonionic surfactant,
  with the proviso that the sum of all surfactant is less than 20% by weight and the composition does not simultaneously comprise 0.01% by weight or more nonionic surfactant and 0.1% by weight or more amphoteric surfactant (including betaine) and/or zwitterionic surfactant and does not simultaneously comprise 0.0% by weight amphoteric and/or zwitterionic surfactant and 0.0% by weight nonionic surfactant,
  wherein the ratio of acyl isethionate to methyl acyl taurate surfactant is between 1.5:1 to 1:1.5, and more preferably, from 1.25:1 to 1:1.25, and preferably, 1.1:1 to 1:1.1, and most preferably, 1:1 and further wherein ratio of surfactant (4) and/or surfactant (5) to anionic surfactant (e.g., components (1) and (2)) is 1:10 to 4:1, preferably, 1:8 to 3:1, more preferably, 1:5 to 2:1, and most preferably, 1:1 with the further proviso that the pH of the composition is 5.0 to 7.4, preferably 6.0 to 7.3.

The invention is described in more detail below.

Fatty acyl isethionates molecules (e.g., cocoyl isethionates) are anionic surfactants highly desirable in personal care skin or hair cleansing products, particularly in personal care products, because they lather well, are mild to the skin and have good emollient properties. Typically, fatty acyl isethionates are produced by direct esterification of fatty acids or by reaction of fatty acid chloride having carbon chain length of C8 to C20 with isethionate. A typical fatty acyl isethionate surfactant "product" (e.g., commercially sold or made surfactant product) contains about 40 to 95 weight % of the fatty acyl isethionate product and 0 to 50 wt. % typically 5 to 40 weight % free fatty acid, in addition to isethionate salts, typically at less than 5%, and trace (less than 2 weight %) of other impurities.

According to our invention, as seen in the examples, when the ratio of methyl acyl taurate to acyl isethionate is 1.5:1 to 1:1.5, preferably 1.25:1 to 1:1.25 and particularly, 1:1 (and other requirements noted are met), the lather volumes are unexpectedly enhanced.

Levels of lather, for purposes of the invention, should be at least of 200 ml, preferably at least 300 ml, when measured at 45 seconds according to the methodology described in the Sita® foam tester below.

A second required component of the claimed invention is methyl acyl taurate. This component is present at a level of 0.1 to 10% by wt., preferably 0.5 to 8% and more preferably 1 to 6% by weight of the total weight of the lamellar composition.

Methyl acyl taurates (or taurides) are a group of mild anionic surfactants. They are composed of a hydrophilic head group, consisting of N-methyltaurine (2-methylaminoethanesulfonic acid) and a lipophilic residue, consisting of a long-chain carboxylic acid (fatty acid), both linked via an amide bond. The fatty acids used could be lauric (C12), myristic (C14), palmitic (C16) or stearic acid (C18), but mainly mixtures of oleic acid (C18:1) and coconut fatty acid (C8-C18) are used. Besides sodium, no other counterions typically play a relevant role (other counterions could be e.g., ammonium or other alkali or alkaline earth metals).

As indicated above, the invention relates to compositions in which the ratio of the acyl isethionate to methyl acyl taurate is 1.5:1 to 1:1.5, preferably 1.25:1 to 1:1.25 and most preferably 1:1. As shown in the examples, at these ratios lather volumes are unexpectedly enhanced.

A third component of the invention is zwitterionic, amphoteric and/or nonionic surfactant, preferably amphoteric surfactant.

Amphoteric surfactants which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

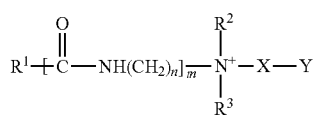

where $R^1$ is alkyl or alkenyl of 7 to 8 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—.

In one embodiment, amphoteric may be alkylamido alkyl betaine (e.g. cocoamidopropyl betaine). It may also be an amphoacetate; or a hydroxy sultaine (e.g., cocoamido propyl hydroxy sultaine).

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy sulfonate, sulfate, phosphate, or phosphonate. A general formula for these compounds is:

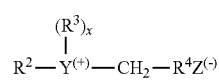

wherein $R^2$ contains an alkyl, alkenyl, or hydroxy alkyl radical of from about 8 to about 18 carbon atoms, from 0 to about 10 ethylene oxide moieties and from 0 to about 1 glycerol moiety; Y is selected from the group consisting of nitrogen, phosphorus and sulfur atoms; $R^3$ is an alky or monohydroxylakyl group containing about 1 to about 3 carbon atoms; X is 1 when Y is a sulfur atom, and 2 when Y is a nitrogen or phosphorous atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

A fourth component of the invention is nonionic surfactant.

The nonionic which may be used includes, in particular, the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

In an embodiment of the invention, the nonionic surfactants used in this invention include lauryl amidopropyl amine oxide, lauramine oxide, cocoamidopropyl amine oxide or mixtures thereof. Such amine oxides are made commercially available from suppliers like Stepan under the Ammonyx name.

In compositions of the invention, the ratio of amphoteric, zwitterionic and/or nonionic surfactant to anionic surfactant is 1:1 to 4:1, preferably 1:1 to 3:1, more preferably, 1.8:1 to 2.2:1.

The liquid compositions may include a variety of other ingredients which are typically found in personal care cleanser compositions.

In addition to the specific isethionate, taurate, and amphoteric/zwitterionic surfactant, the compositions may comprise small amounts of additional surfactants (typically used in an amount less than any of the three surfactants) as long as total amount of all surfactants is less than 20% by weight of the lamellar liquid cleansing composition of this invention.

Other surfactants that may optionally be included are cationic surfactants as described in U.S. Pat. No. 3,723,325 to Parran Jr. and "Surface Active Agents and Detergents" (Vol. I & II) by Schwartz, Perry & Berch, the disclosures of both are incorporated into the subject application by reference.

The composition of the invention utilizes from 0.1 to 20%, preferably 1 to 10%, more preferably 2 to 5% by weight of a lamellar structuring agent (based on total weight of the lamellar liquid cleansing composition) which works in the compositions to form a lamellar phase. Such lamellar phase enables the compositions to suspend particles more readily (e.g., emollient particles) while still maintaining good shear thinning properties. The lamellar phase also provides consumers with desired rheology ("heaping").

Examples of fatty acids (or ester derivative, thereof, a fatty alcohol, or trihydroxystearin), which may be used as structurants are $C_8$-$C_{22}$ acids such as the following: caprylic acid, lauric acid, myristic acid, oleic acid, isostearic acid, linoleic acid, linolenic acid, ricinoleic acid, elaidic acid, arachidonic acid, myristoleic acid and palmitoleic acid, and the like. Ester derivatives include propylene glycol isostearate, propylene glycol oleate, glyceryl isostearate, glyceryl oleate and polyglyceryl diisostearate, and the like.

The structurant is preferably a fatty acid. More preferably, the structurant is selected from the group consisting of caprylic acid, lauric acid, myristic acid or a mixture thereof.

Water soluble/dispersible polymers are an optional ingredient that is often preferred to be included in the liquid composition of the invention in order to contribute to the stability of the lamellar composition. The water soluble/or dispersible polymers can be cationic, anionic, amphoteric or nonionic polymers with a molecular weight higher than 100,000 Daltons. These polymers are known to enhance in-use and after-use skin sensory feel, to enhance lather creaminess and lather stability, and to increase the viscosity of liquid cleanser compositions.

Such polymers make up from 0.05 to 6%, and preferably, from 0.1 to 4% by weight of the total weight of the lamellar composition.

Examples of water soluble/or dispersible polymers useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum Arabic, gum acacia, gum agar, xanthan gum and mixtures thereof; modified and nonmodified starch granules with gelatinization temperature between 30 to 85° C. and pregelatinized cold water soluble starch; polyacrylate; Carbopols; alkaline soluble emulsion polymer such as Aculyn 28, Acuyln 22 or Carbopol Aqua SF1; cationic polymer such as modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance 3000, N-Hance 3196, N-Hance GPX 215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Galactasol 800 series by Henkel, Inc.; Quadrosoft Um-200; and Polyquaternium-24.

Gel forming polymers such as modified or non-modified starch granules, xanthan gum, Carbopol, alkaline-soluble emulsion polymers and cationic guar gum such as Jaguar C13S, and cationic modified cellulose such as UCARE Polymer JR 30 or JR 40 are particularly preferred for this invention.

Water Soluble and Water Insoluble Skin Benefit Agents

Water-soluble skin benefit agents are an often preferred optional ingredient suitable to be included in the liquid compositions of the invention. A variety of water-soluble skin benefit agents can be used, and the level can be from 0 to 40%, preferably 1 to 30%, and even more preferable 2 to 12% by weight. The materials include, but are not limited to, polyhydroxy alcohols such as glycerol, propylene glycol, sorbitol, panthenol and sugar; urea, alpha-hydroxy acid and its salt such as glycolic or lactic acid, and low molecular weight polyethylene glycols with molecular weight less than 20,000. Preferred water-soluble skin benefit agents for use in the liquid compositions are glycerol, sorbitol and propylene glycol.

One class of ingredients are nutrients used to moisturize and strengthen, for example, the skin. These include:
  a) vitamins such as vitamin A and E, and vitamin alkyl esters such as vitamin C alkyl esters;
  b) lipids such as cholesterol, cholesterol esters, lanolin, ceramides, sucrose esters, and pseudo-ceramides;
  c) liposome forming materials such as phospholipids and suitable amphophilic molecules having two long hydrocarbon chains;
  d) essential fatty acids, poly unsaturated fatty acids, and sources of these materials;
  e) triglycerides of unsaturated fatty acids such as sunflower oil, primrose oil avocado oil, almond oil;
  f) vegetable butters formed from mixtures of saturated and unsaturated fatty acids such as Shea butter;
  g) minerals such as sources of zinc, magnesium, and iron.

A second type of skin benefit agent that is water insoluble is a skin conditioner used to provide a moisturized feel to the skin. Suitable skin conditioners include:
  a) silicone oils, gums and modifications thereof such as linear and cyclic polydimethylsiloxanes, amino, alkyl, and alkyl aryl silicone oils;
  b) hydrocarbons such as liquid paraffins, petrolatum, Vaseline, microcrystalline wax, ceresin, squalene, pristan, paraffin wax and mineral oil;
  c) conditioning proteins such as milk proteins, silk proteins and glutens;
  d) cationic polymers as conditioners which may be used include Quatrisoft LM-200 Polyquaternium-24, Merquat Plus 3330-Polyquaternium 30; and Jaguar® type conditioners;
  e) humectants such as glycerol, sorbitol, and urea;
  f) emollients such as esters of long chain fatty acids, such as isopropyl palmitate and cetyl lactate.

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:
  a) antimicrobials such as 2-hydrozy-4,2',4'-trichlorodiphenylether (DP300) 2,6-dimeth-4-hydroxychlorobenzene (PCMX), 3,4,4'-trichlorocarbanilide (TCC), 3-trifluoromethyl-4,4'-dichlorocarbanilide (TFC), benzoyl peroxide, zinc slats, tea tree oil,
b) anti-acne agents such as salicylic acid, lactic acid, glycolic acid, and citric acid, and benzoyl peroxide (also an antimicrobial agent),
c) oil control agents including sebum suppressants, modifiers such as silica, titanium dioxide, oil absorbers, such as micro sponges,
d) astringents including tannins, zinc and aluminum salts, plant extracts such as from green tea and Witch-hazel (Hammailes),
e) scrub and exfoliating particles, such as polyethylene spheres, agglomerated silica, sugar, ground pits, seeds, and husks such as from walnuts, peach, avocado, and oats, salts,
f) cooling agents such as methanol and its various derivatives and lower alcohols,
g) fruit and herbal extracts,
h) skin calming agent such as aloe vera,
i) essential oils such as metah, jasmine, camphor, white cedar, bitter orange peel, rye, turpentine, cinnamon, bergamot, citrus unshiu, calamus, pine, lavender, bay, clove, hiba, eucalyptus, lemon, starflower, thyme, peppermint, rose, sage, menthol, cineole, sugenol, citral, citronelle, borneol, linalool, geraniol, evening primrose, camphor, tymol, spirantol, penene, limonene and terpenoid oils.

Other benefits agents that can be employed include anti-aging compounds, sunscreens, and lightening agents and benefit agents like vitamin B3, resorcinols (especially 4-substituted resorcinols like 4-ethyl and 4-hexyl resorcinol), retinoids, as well as antimicrobial agents like terpineol and/or thymol.

When the benefit agent is oil, especially low viscosity oil, it may be advantageous to pre-thicken it to enhance its delivery. In such cases, hydrophobic polymers of the type described in U.S. Pat. No. 5,817,609 to He et al. may be employed, the disclosure of which is incorporated by reference into the subject application.

The final liquid cleanser composition of the present invention should have pH from 5.0 to 7.4, preferably 6.0 to 7.3. At ambient temperature, the composition contains surfactant crystals with dissolution temperature between 30° C. to 50° C. The compositions should also be physically phase stable at room temperature and 45° C. for at least two weeks.

Other Optional Components

In addition, the compositions of the invention may include 0 to 10% by wt. optional ingredients as follows:

Perfumes; sequestering agents, such as tetra sodium ethylenediaminetetraacetate (EDTA), EHDP or mixtures in an amount of 0.01 to 1%, preferably 0.01 to 0.05%; and coloring agents, opacifiers and pearlizers such as zinc striate, magnesium stearate, $TiO_2$, EGMS (ethylene glycol monostearate) or Lytron 621 (styrene/acrylate copolymer); all of which are useful in enhancing the appearance of cosmetic properties of the product.

The compositions may further comprise antimicrobials such as 2-hydroxy-4,2'4' trichlorodiphenyl ether (DP300); preservatives such as dimethylodimethylhydantoin (Glydant XL 1000), parabens, phenoxyethanol, hydroxyacetophenone, sorbic acid, or the like. The efficacy of such preservatives can be boosted with well know ingredients classified as alkane diols like 1,2-octane diol, 1,2-pentane diol, 1,2-hexane diol or a mixture thereof.

Antioxidants such as, for example, butylated hydroxytoluene (BHT) and/or EDTA may be used advantageously in amounts of about 0.01% or higher if appropriate.

Polyethylene glycols as conditioners which may be used include:

| Polyox | WSR-25 | PEG 14M, |
|---|---|---|
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

The invention further comprises method of preparing compositions comprising components of the compositions noted above, wherein the ratio of acyl isethionate to acyl methyl taurate is 1.5:1 to 1:1.5, preferably 1.25:1 to 1:1.25; wherein ratio of amphoteric, zwitterionic and/or nonionic surfactant to anionic surfactant is 0.1:1 and higher; and wherein the sum of surfactants is less than 20% by wt., which method comprises:

A first step may include mixing primary surfactants with the structurant at 65-75° C. to deionized water. Subsequently, auxiliary thickeners, stabilizers, emollient oils and antioxidants were added. The batch was mixed to a uniform consistency and then cooled to 35° C. Co-surfactants were added during cooling, followed by skin conditioners, humectants, chelating agents, pH adjusters, preservatives, fragrance and other sensitives between 35-45° C.

The invention further comprises use of compositions of the invention to enhance lather.

Compositions of the invention are lamellar in character.

The Examples provided are to further illustrate an understanding of the invention. The Examples are not intended to limited the scope of the claimed invention.

EXAMPLES AND PROTOCOL

In all the ensuing examples the lather was created using a Sita Foam apparatus and the procedure is shown below.

Various dilutions of product with water, ranging from 2.5 grams of product to 250 grams of water to 10 grams of product to 250 grams of water since consumers typically use a range of product amounts in the shower and the dilution used in these examples approximates such range. Additionally, consumers may also apply and rub products on the skin, either with the hand or pouf, with different force and to approximate such variability some of the tests were run at two different stirrer speeds.

Sita Foam Tester R-2000 Procedure

The Sita Foam (Sita Foam Tester R-2000) was used to measure foam generation under a specified dilution and shear rate. It utilizes a rotor at high speeds which both mixes the product with dilution water, and creates lather volume. The rotor creates a vortex, which incorporates air; lathering at different rates depending on the ability of the formulation. To operate the Sita Foam, the measurement parameters are into the application in the "Device" drop down menu. See the table below for the parameters used during these measurements.

| Parameter | Series Count | Fill with | Stir Counts | Stir Time | Revolution |
|---|---|---|---|---|---|
| | | | Foam Build Up Measurement | | |
| Medium Shear Test | 1 | 250 mL | 4 | 15 s | 1000 min$^{-1}$ |
| High Shear Test | 1 | 250 mL | 4 | 15 s | 1500 min$^{-1}$ |

A heat exchanger should be connected to the Sita Foam's glass vessel to ensure a consistent temperature throughout the testing. Set the heat exchanger to 38 Celsius, and wait 15 minutes for the temperature to reach 38° C. Fluctuation of the temperature in the heat exchanger between 37° C. and 39° C. is acceptable.

Dispense 1 g, 2.5 g, 5 g, or 10 g of product into the Sita Foam glass vessel, ensuring that the product does not land on the sides of the vessel or on the rotor, which can cause inaccuracy in the readings. Then add water to the holding tank in the back of the Sita Foam. Adjust the water temperature to between 37° and 39° C. This water will be used to dilute the product and generate lather.

Start the run on the Sita Foam. The Sita Foam will automatically dilute the product, then mix for 15 seconds. The run mixes four separate times, taking a measurement between each reading. At least three readings should be taken for each unique sample at each dilution desired.

Readings below 300 mL of foam generation are not to be considered due to susceptibility to error for reliable evaluation. If the standard error at 2.5 g and 5 g is too high to discern differentiation, increase product dosing to 10 g, or change parameters to those seen in the high shear test using 1 g of product.

EXAMPLES

TABLE 1

Methyl Acyl Taurate - Acyl Isethionate surfactant System - Composition

| Chemical | Minimum (Active %) | Maximum (Active %) |
|---|---|---|
| DI Water | Q.S. | Q.S. |
| Sodium Hydroxypropyl Starch Phosphate | 4.5 | 4.5 |
| Sodium Lauroyl Isethionate | 0 | 6 |
| Sodium Methyl Lauroyl Taurate | 0 | 6 |
| Stearic Acid | 0.25 | 0.25 |
| Butylated Hydroxytoluene | 0.1 | 0.1 |
| Hydrogenated Soybean Oil | 2.1 | 2.1 |
| Glycine Soja (Soybean) Oil | 0.9 | 0.9 |
| Lauric Acid | 3.0 | 3.0 |
| Cocamidopropyl Betaine | 6.00 | 6.00 |
| Guar Hydroxypropyltrimonium Chloride | 0.36 | 0.36 |
| Glycerin | 0.88 | 0.88 |
| Tetrasodium EDTA | 0.05 | 0.05 |
| Citric Acid | 0.10 | 0.59 |
| Sodium Hydroxide | 0.36 | 0.49 |
| Phenoxyethanol | 0.6 | 0.6 |
| Iodopropynyl Butylcarbamate | 0.007 | 0.007 |
| Fragrance | 1.00 | 1.00 |

TABLE 1A

Methyl Acyl Taurate - Acyl Isethionate surfactant System - Lather Volume

| Dilutions Sodium Methyl Lauroyl Taurate/Sodium Lauroyl Isethionate (Wt. %/Wt. %) | 5.0 g/250 mL, 1000 RPM Foam Volume (mL) at 45 Sec. | STD. Error |
|---|---|---|
| 0.0%/100.0% | Unstable | Unstable |
| 33.3%/66.7% | 433 | 6 |
| 50.0%/50.0% | 519 | 8 |
| 66.7%/33.3% | 424 | 8 |
| 100.0%/0.0% | Unstable | Unstable |

This table shows that a synergistic improvement in lather volume is obtained at a ratio of methyl acyl taurate to acyl isethionate of 1:1. Both the 100% isethionate and the 100% Taurate examples showed instability (formula separation, not homogeneous), and thus were not included in the analysis.

TABLE 2

T Methyl Acyl Taurate-Acyl Isethionate-Acyl Glycinate Surfactant System - Composition

| Chemical | Minimum (Active %) | Maximum (Active %) |
|---|---|---|
| DI Water | Q.S. | Q.S. |
| Sodium Hydroxypropyl Starch Phosphate | 2.00 | 2.00 |
| Sodium Cocoyl Isethionate | 0.00 | 6.00 |
| Sodium Methyl Lauroyl Taurate | 0.00 | 6.00 |
| Sodium Cocoyl Glycinate | 2.60 | 2.60 |
| Stearic Acid | 0.25 | 0.25 |
| Butylated Hydroxytoluene | 0.10 | 0.10 |
| Hydrogenated Soybean Oil | 1.80 | 1.80 |
| Helianthus Annuus (Sunflower) Seed Oil | 1.20 | 1.20 |
| Pemulen TR1 | 0.25 | 0.25 |
| Lauric Acid | 2.77 | 2.77 |
| Cocamidopropyl Betaine | 3.30 | 3.30 |
| Guar Hydroxypropyltrimonium Chloride | 0.36 | 0.36 |
| Glycerin | 1.00 | 1.00 |
| Tetrasodium EDTA | 0.05 | 0.05 |
| Citric Acid | 0.05 | 0.11 |
| Sodium Hydroxide | 0.15 | 0.18 |
| Phenoxyethanol | 0.60 | 0.60 |
| Iodopropynyl Butylcarbamate | 0.007 | 0.007 |
| Fragrance | 1.20 | 1.20 |

TABLE 2A

Methyl Acyl Taurate-Acyl Isethionate- Acyl Glycinate Surfactant System- Lather Volume

| Dilutions Sodium Mehtyl Lauroyl Taurate/ Sodium Cocoyl Isethionate (Wt.%/Wt.%) | 5.0 g/250 mL, 1000 RPM Foam Volume (mL) at 45 Sec. | STD. Error |
|---|---|---|
| 0.0%/100.0% | Unstable | Unstable |
| 25.0%/75.0% | 462 | 2 |
| 40.0%/60.0% | 467 | 10 |
| 50.0%/50.0% | 502 | 13 |
| 60.0%/40.0% | 481 | 2 |
| 75.0%/25.0% | 440 | 15 |
| 100.0%/0.0% | Unstable | Unstable |

The synergistic behavior of acyl methyl taurate and acyl isethionate also occurs in formulations containing the anionic surfactant, acyl glycinate, which was maintained at a constant level (2.6%). Both the 100% isethionate and the 100% taurate examples showed instability (formula separation, not homogeneous), and thus were not included in the analysis.

The invention claimed is:

1. A liquid lamellar composition comprising:
   1) 0.1 to 10% by weight of acyl isethionate comprising sodium lauroyl isethionate;
   2) 0.1% to 10% by weight of a methyl acyl taurate comprising sodium methyl lauroyl taurate, sodium methyl cocoyl taurate or a mixture thereof;
   3) 0.1 to 20% by weight structurant comprising caprylic acid, lauric acid, myristic acid or a mixture thereof;
   4) 0.1 to 10% by weight of a zwitterionic surfactant comprising cocamidopropyl betaine; and
   5) 0.0 to 8.0% by weight nonionic surfactant, wherein the zwitterionic surfactant comprises cocamidopropyl betaine, with the proviso that surfactant is at a sum of less than 20% by weight and the composition does not simultaneously comprise 0.0% by weight zwitterionic surfactant and 0.9% by weight nonionic surfactant, and further wherein the weight ratio of methyl acyl taurate to acyl isethionate surfactant is between 1.1:1 to 1:1.15, the composition has 0 to 15% by weight glycerol, a pH from 6 to 7.3, less than 0.2% by weight sulfate-based surfactant, a preservative and a structurant comprising caprylic acid, lauric acid, myristic acid or a mixture thereof.

2. The composition according to claim 1 wherein the weight ratio of zwitterionic surfactant plus nonionic surfactant to anionic surfactant is 1:10 to 4:1.

3. The composition according to claim 1 wherein the composition pH iso 6.3 to 7.3, and further wherein the composition comprises less than 0.01 percent by weight nonionic surfactant.

4. The composition according to claim 1 wherein the weight ratio of zwitterionic surfactant plus nonionic surfactant to anionic is 1:5 to 2:1.

5. The composition according to claim 1 wherein nonionic surfactant is present.

6. The composition according to claim 5 wherein the nonionic surfactant is cocoamidopropyl amine oxide.

7. The composition according to claim 1 wherein the structurant is lauric acid making up from 0.5 to 8% by weight of the composition.

8. The composition according to claim 1 wherein the composition comprises from 1 to 6%, by weight of acyl isethionate.

9. The composition according to claim 1 wherein the composition comprises from 1 to 6% by weight of methyl acyl taurate comprising lauroyl methyl taurate, cocoyl methyl taurate or a mixture thereof.

10. The composition according to claim 1 wherein the composition comprises from 1 to 10% by weight structurant comprising caprylic acid, lauric acid, myristic acid or a mixture thereof.

11. The composition according to claim 1 wherein the composition comprises from 0.5 to 8% by weight of the zwitterionic surfactant.

12. The composition according to claim 1 wherein the composition comprises from 0.001 to 7.0% by weight nonionic surfactant.

13. The composition according to claim 1 wherein the composition comprises from 0.02 to 10% by weight glycerol.

14. The composition according to claim 1 wherein the composition comprises less than 0.2% by weight sulfate-based surfactant.

15. The composition according to claim 1 wherein the composition comprises from 0.0001 to less than 0.2% by weight sulfate-based surfactant.

16. The composition according to claim 1 wherein the composition comprises less than 3% by weight betaine and has 0.0% by weight sulfate-based surfactant.

17. The composition according to claim 1 wherein the composition further comprises from 0.05 to 6% by weight of cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum Arabic, gum acacia, gum agar, xanthan gum, polyacrylate, modified polysaccharide or a mixture thereof.

18. The composition according to claim 1 wherein the composition further comprises silicone oil, liquid paraffins, petrolatum, microcrystalline wax, ceresin, squalene, paraffin wax, mineral oil, plant extract, green tea, isopropyl palmitate, cetyl lactate, tea tree oil or a mixture thereof.

19. The composition according to claim 1 wherein the composition further comprises glycerol, stearic acid and palmitic acid.

* * * * *